(12) United States Patent
Liu et al.

(10) Patent No.: US 6,248,069 B1
(45) Date of Patent: Jun. 19, 2001

(54) ULTRASOUND IMAGING SYSTEM AND METHOD USING A QUANTUM WELL-DEVICE FOR ENABLING OPTICAL INTERCONNECTIONS

(75) Inventors: Yung Sheng Liu, Hsinchu (TW); Lowell Scott Smith, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/699,099

(22) Filed: Oct. 30, 2000

(51) Int. Cl.$^7$ ........................................ A61B 8/00
(52) U.S. Cl. ...................... 600/437; 600/459; 365/151
(58) Field of Search ..................... 600/443, 447, 600/438, 437; 365/151, 158, 170

(56) References Cited

U.S. PATENT DOCUMENTS

| | | |
|---|---|---|
| 5,203,335 | 4/1993 | Noujaim et al. . |
| 5,237,529 * | 8/1993 | Spitzer ................................. 365/158 |
| 5,353,262 | 10/1994 | Yakymyshyn et al. . |
| 5,393,375 * | 2/1995 | MacDonald et al. ................ 156/643 |
| 5,565,867 | 10/1996 | Tiemann . |
| 5,590,090 | 12/1996 | Duggal et al. . |
| 5,592,413 * | 1/1997 | Spitzer ................................. 365/151 |
| 5,732,046 | 3/1998 | O'Donnell et al. . |

OTHER PUBLICATIONS

R.A. Novotny, et al., titled "Field Effect Transistor–Self Electro-optic Device Data Links" Journal of Lightwave Technology. vol. 13, p. 606, 1995.

H.S. Hinton and A. L. Lentine, "Multiple Quantum–Well Technology Takes SEED" IEEE, Circuit and Deviceds, p. 12, 1993.

K. W. Goossen, et al., titled GaAs MQW Modulators Integrated with Silicon CMOS, IEEE Photonics Technology Letters, vol. 7, No. 4, Apr. 1995.

James D. Hamilton, et al., titled High Frequency Ultrasound Imaging Using an Active Optical Detector, IEEE Transactions on Ultrasonics, Ferroelectrics, and Frequency Control, vol. 45, No. 3, May 1998.

Charles D. Emery, et al., titled Optoelectronic Transmitter for Medical Ultrasound Transducers, IEEE Transactions on Ultrasonics, Ferroelectrics, and Frequency Control, vol. 42, No. 2 Mar. 1995.

* cited by examiner

Primary Examiner—Marvin M. Lateef
Assistant Examiner—Maulin Patel
(74) Attorney, Agent, or Firm—Ann M. Agosti; Jill M. Breedlove

(57) ABSTRACT

An ultrasound imaging system having an ultrasonic probe including an array of ultrasonic transducers is provided. The imaging system further includes a plurality of interconnect channels for enabling optical communication of the ultrasonic probe with an imaging console. Each interconnect channel includes a quantum-well device having a terminal electrically coupled to receive an electrical signal from a corresponding transducer. The quantum well device is further configured to receive and process an input optical signal to supply a modulated optical signal in response to amplitude variation of the electrical signal. An optical cable assembly is coupled to transmit from the imaging console the optical input signal received by the quantum-well device.

25 Claims, 2 Drawing Sheets

ULTRASOUND IMAGING SYSTEM AND METHOD USING A QUANTUM WELL-DEVICE FOR ENABLING OPTICAL INTERCONNECTIONS

BACKGROUND OF THE INVENTION

The present invention is generally related to ultrasound systems, and, more particularly, the present invention is related to optical interconnect and method for optically coupling an ultrasonic probe and an imaging console using a quantum-well device.

Ultrasound systems typically comprise a hand-held probe having an array of ultrasound transducer elements which transmit during a transmit mode of operation a vibratory signal to be propagated into a medium and receive during a receive mode of operation a reflected signal from within the medium. By controlling the time delay and the applied voltages of an array of such transducers, the focal point of an ultrasound beam can be controlled and scanned. A transducer array can be used both as a transmitter and receiver. It thus forms an image by properly controlling the beam-forming parameters.

In known ultrasound array imaging systems, each transducer element is commonly connected by an individual miniaturized coaxial cable to a single analog channel followed by an analog-to-digital converter and delay circuit. Thus, for example, a 128-channel system may use up to 128 delay circuits plus all other associated electronic components. At typical imaging frequencies of 1–20 MHz, delay circuits need timing accuracy in the order of a few nanoseconds. The transducer array may be assembled separately from the console electronics unit which provides the electrical control, signal processing, and power conditioning. The interconnect between the transducer unit and the electronic unit becomes complicated as the number of array elements increases. For example, the large number of individual coaxial cables collectively becomes difficult to maneuver. The degree of complexity increases even more as the sensor array becomes two dimensional (2D) for three dimensional (3D) or volumetric scanning. Sometimes additional components, such as multiplexers, may be installed in the probe to attempt to reduce the cable count. Unfortunately, the additional components may increase the cost of the imaging system and may impact the overall reliability of the system.

Previous attempts to use optical fibers to communicate ultrasound information are believed to have been generally based on one of the following two techniques. In the first known technique, the received echo signal is used to drive an optical source. Unfortunately, such optical sources typically have relatively low efficiency and hence they result in high power consumption devices. For example, the amount of power dissipated in a probe handle may be prohibitive since it may result in exceeding heat dissipation constraints. In the second known technique, the power dissipation in the handle is reduced by putting the optical source in the console, and then modulating the signal from that optical source with information from the acoustic echo. Unfortunately, this technique is also believed to have failed to provide a practical solution since such technique also results in relatively high power consumption, very low dynamic range, or both. For example, a standard Mach-Zehnder modulator may dissipate in the order of one watt.

In view of the foregoing issues, it would be desirable to provide systems and techniques that could reduce the complexity of the interconnects and cabling in ultrasound probes, such as multirow or two-dimensional (2D) ultrasound transducer arrays. It would be further desirable to provide a greatly improved optical modulator that has a relatively high dynamic range and that further allows for relatively low power dissipation in the operation of the imaging system so as to handle operation of a large number of channels using an optical fiber interconnect.

BRIEF SUMMARY OF THE INVENTION

Generally speaking, in one exemplary embodiment of the present invention, the foregoing needs are fulfilled by providing an ultrasound imaging system comprising an ultrasonic probe including an array of ultrasonic transducers. The imaging system further comprises a plurality of interconnect channels for enabling optical communication of the ultrasonic probe with an imaging console. Each interconnect channel comprises a quantum-well device having a terminal electrically coupled to receive an electrical signal from a corresponding transducer. The quantum well device is further configured to receive and process an input optical signal to supply a modulated optical signal in response to amplitude variation of the electrical signal. An optical cable assembly is coupled to transmit from the imaging console the optical input signal received by the quantum-well device.

The present invention further fulfills the foregoing needs by providing in another aspect thereof an optical interconnect for an ultrasound imaging system having an ultrasonic probe including an array of ultrasonic transducers. The interconnect comprises a plurality of interconnect channels for enabling optical communication of the ultrasonic probe with an imaging console. Each interconnect channel comprises a quantum-well device having a terminal electrically coupled to receive an electrical signal from a corresponding transducer. The quantum well device is further configured to receive and process an input optical signal to supply a modulated optical signal in response to amplitude variation of the electrical signal. A first optical cable assembly is coupled to transmit from the imaging console the optical input signal received by the quantum-well device. The first optical cable assembly is further coupled to transmit back to the imaging console the modulated signal supplied by the quantum well device. A second optical cable assembly is coupled to a phototransistor circuit responsive to an optical control signal transmitted from the console through said second optical cable assembly to generate a respective excitation electrical signal, wherein said excitation electrical signal is transmitted to a corresponding transducer to cause the transducer to generate vibratory energy to be propagated through a medium during a transmit mode of operation of the ultrasound system, and further wherein the electrical signal received by the quantum-well device from each corresponding transducer is generated during a receive mode of operation of the ultrasound system in response to propagated vibratory energy received from within the medium.

In yet another aspect of the present invention, the foregoing needs are fulfilled by providing a method for optically interconnecting an ultrasound imaging system having an ultrasonic probe including an array of ultrasonic transducers. The method allows for enabling optical communication of the ultrasonic probe with an imaging console through a plurality of interconnect channels. The method further allows for electrically coupling a quantum-well device to receive an electrical signal from a corresponding transducer. A coupling step allows for optically coupling the quantum well device to receive and process an input optical signal to supply a modulated optical signal in response to amplitude variation of the electrical signal. An optical cable assembly is provided to transmit from the imaging console the optical input signal received by the quantum-well device. A coupling step allows for optically coupling that first optical cable assembly to transmit back to the imaging console the modulated signal supplied by the quantum well device.

Figure 1:
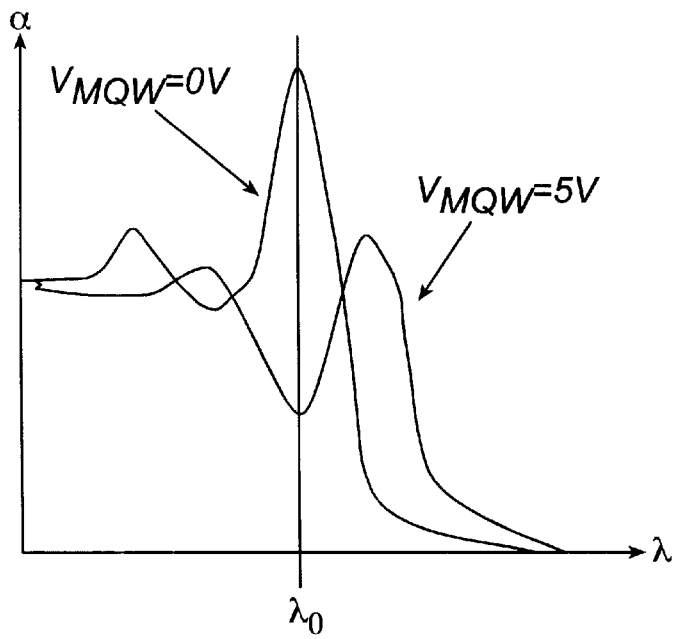
FIG. 1 shows respective exemplary plots illustrating spectral absorption characteristics of a quantum-well device as a function of a voltage signal applied across the device.

Before any embodiment of the invention is explained in detail, it is to be understood that the invention is not limited in its application to the details of construction and the arrangements of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

DETAILED DESCRIPTION OF THE INVENTION

For facility of understanding of one of the key components of the present invention, the reader is provided below with a brief synopsis regarding various aspects of quantum-well devices, that is, electro-optic semiconductor devices. As will be appreciated by those skilled in the art, a quantum-well device generally comprises a double heterojunction structure made up of a relatively thin (e.g., less than 50 nm) layer of semiconductor material whose bandgap is smaller than that of the surrounding material. An example is provided by a thin layer of GaAs (gallium arsenide) surrounded by AlGaAs (aluminum gallium arsenide). Another example of an electro-optic semiconductor device is the self-electro optic (SEED) device. The SEED device uses a heterostructure multiquantum well semiconductor material comprising by way of example, multiple alternating layers of relatively narrow and wide bandgap materials, such as GaAs and AlGaAs.

Quantum confinement of carriers in the quantum wells leads to the formation of distinct peaks in the absorption spectrum. When a voltage is applied across such a quantum well device it acts as a diode and the position of the peaks shift as a result of the electro-absorption mechanism, the so-called quantum confined Stark effect as shown in FIG. 1. The effect is so remarkable that for example, a 5 volt change across a 1 $\mu$m thick multiple quantum well will change the absorption by a factor of two. Based on this effect, 2D array optical modulators may be fabricated. For readers desiring further background information, see for example, article by R. A. Novotny, et al., titled "Field Effect Transistor-Self Electro-optic Device (FET-SEED) Differential Transimpedance Amplifiers for Two-Dimensional Optical Data Links" Journal of Lightwave Technology. Vol. 13, p. 606, 1995. A typical device may have an operating voltage of 5–10 V with an optical transmission change from 20% to 50%. The device can be operated in transmission or reflection mode. The latter can be achieved by incorporating a mirror into the diode structure, so that light may be reflected from the bottom of the device. This type of device typically operates at frequencies on the order of several gigahertz, which are relatively fast compared to typical diagnostic ultrasound frequencies.

In addition to their large changes in optical absorption, the SEED devices may be configurable to be combined with various types of semiconductor circuits, such as Complementary Metal Oxide Semiconductor (CMOS) or Field Effect Transistor (FET) electronics to form hybrid structures. See for example, article by H. S. Hinton and A. L. Lentine, "Multiple Quantum-Well Technology Takes SEED" IEEE, Circuit and Devices, p. 12, 1993, for a detailed perspective regarding the development of quantum well devices, such as "self-electro-optic effect devices" (SEEDs). It will be appreciated that some of the initial efforts regarding SEED devices focused on integrating the SEED device with CMOS circuitry to perform smart pixel functions for 2D optical interconnect input/output. It will be thus appreciated that there are techniques well-understood by those of ordinary skill in the art, that, for example, would allow for bonding a SEED device onto a CMOS substrate and integrating optical inputs and outputs to standard silicon-based CMOS circuitry. The optical inputs and outputs are provided using quantum well diodes which can operate either as optical reflective modulators or as photodiodes.

Figure 2:
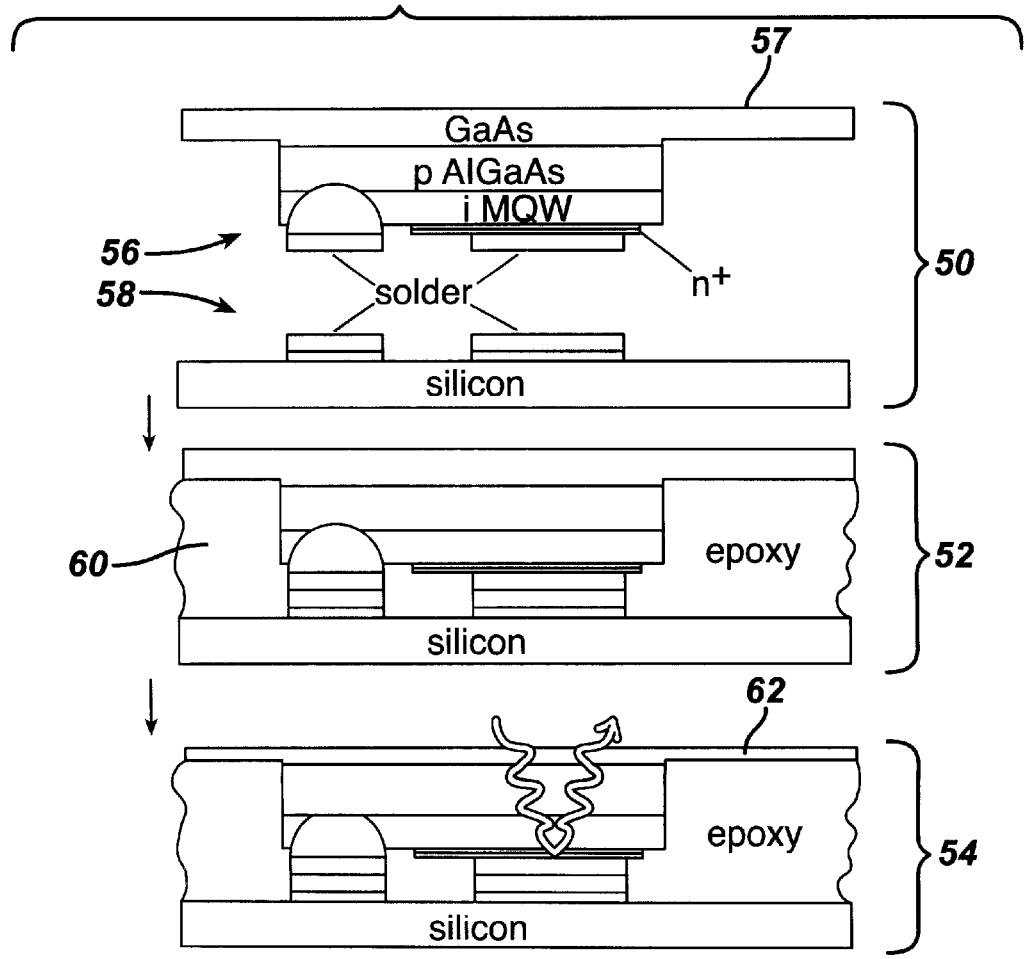
FIG. 2 illustrates exemplary assembly of a quantum-well device, such as a self-electro-optic effect (SEED) device integrated with a semiconductor circuit.

Various exemplary assembly actions or steps that may be used for integrating the SEED device and the CMOS circuitry are sequentially shown in FIG. 2. As shown at step 50, an array of SEED diodes 56 on a GaAs substrate 57 may be aligned relative to an array of silicon-based circuits 58 to be bonded and electronically connected in a regular grid on top of the array of circuits 58 where the modulators include the multiple thin layers. The array of diodes can be fabricated in a quantum well p-i-n diode wafer grown by molecular beam epitaxy and then, as shown at step 52, these diodes are solder-bonded to the silicon chip and further held in position with epoxy 60, for example. As shown at step 54, the entire GaAs substrate is removed, and the diodes are coated with an anti-reflection coating 62 on the top surface. The epoxy over the silicon circuit is also removed (not shown) to allow access to electrical bond pads. It will be appreciated there are commercially available foundries that can be used for the design and fabrication of user-specific SEED devices, such as the SEED foundry established at the Bell Laboratories of Lucent Technologies.

Figure 3:
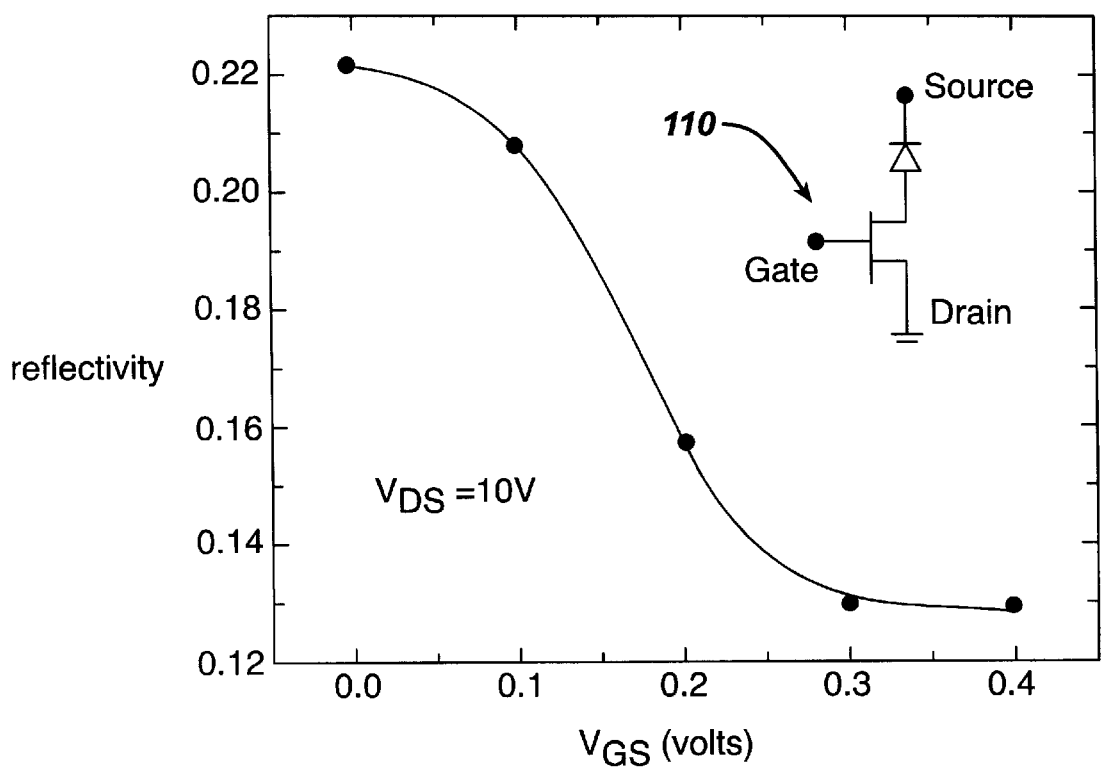
FIG. 3 shows an exemplary plot of optical reflectivity of a SEED device as a function of a voltage applied at its gate terminal, assuming an exemplary biasing voltage of 10 volts is applied at its source terminal.

As suggested above, SEED devices have been hybridly integrated with silicon-based CMOS and have been used as optical modulators. For example as shown in FIG. 3, the reflectivity of a SEED device used as a modulator can be changed from about 0.22 to about 0.13 when the gate-source voltage is increased from about 0 to about 0.4 volts. The inventors of the present invention have recognized that this type of electro-optic semiconductor device could be used as an interconnect for coupling optical signals with an ultrasound transducer. As described in greater detail below, one exemplary approach is to use a SEED modulator in conjunction with a CMOS circuit coupled to the ultrasound transducer. The electrical signal generated by the ultrasound transducer can be used to modulate the optical reflectivity of the SEED device. For example, referring to the inset circuit 110 shown in FIG. 3, this could mean that the electrical signal from the transducer is applied to the gate terminal of the circuit and the source terminal is connected to a suitable biasing signal while the drain terminal is connected to an electrical ground.

In another exemplary approach, one may connect the ultrasound transducer in the array with a reversed biased photo-diode in series with a quantum well device. When the diode is reverse biased, the electric field is applied to the quantum well with virtually no current flowing through. When the reversed biased voltage is changed, this would change the field applied to the quantum wells, and thus modulate the optical beam intensity. Once again, referring to the inset circuit shown in FIG. 3, this would mean that the electrical signal is applied to the source terminal of the circuit and the gate terminal would be connected to the biasing signal while the drain terminal is connected to the electrical ground. Thus, it will be appreciated that, depending on the specific design, one may electrically couple the three terminals in various ways to achieve the same result, namely, to vary the reflectivity of the SEED device as a function of amplitude variation of the electrical signal supplied from the ultrasound transducer.

As suggested above, in a traditional transducer array, each individual transducer element is electrically connected to the console electronics by a coaxial cable. The cable transmits a high voltage excitation signal which causes the transducer element to transmit vibratory energy into a medium during a transmission mode of operation. During a receive mode of operation, the cable then receives a low voltage signal which corresponds to the received sound waves picked up by the transducer elements. Although individually of small diameter, e.g., these coaxial cables are typically 400 microns in diameter, collectively the overall cabling size may become bulky. For example, assuming a bundle of 500 cables, then the overall size of the cabling may be about 1.5 cm or more in diameter. One major benefit of the proposed invention is to reduce the size and mass of this connecting cable bundle, by replacing the coaxial electrical cables with an optical cable assembly.

Figure 4:
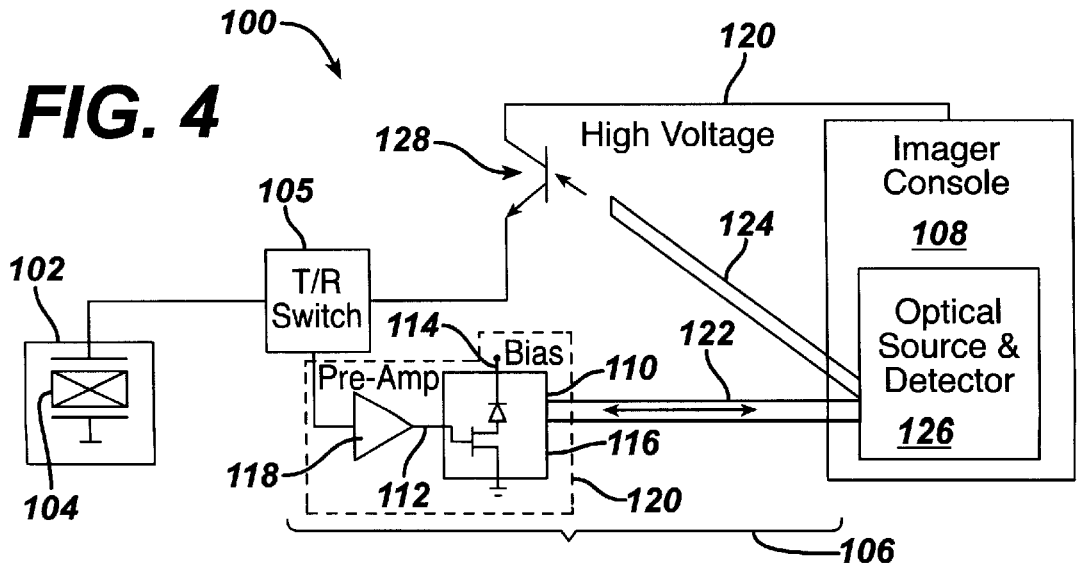
FIG. 4 is a schematic representation of an ultrasound system using an exemplary optical interconnect in accordance with one aspect of the present invention.

FIG. 4 shows an exemplary embodiment of an ultrasound imaging system 100 embodying one aspect of the present invention. Imaging system 100 includes an ultrasonic probe 102 including an array of transducers, for simplicity of illustration only one ultrasonic transducer 104 is shown, responsive to a relatively high voltage excitation signal that causes the transducer to generate vibratory energy. It will be appreciated by those skilled in the art that the present invention is not be limited to any specific type of transducer array. For example, in one exemplary embodiment any standard piezoelectric transducer array may be used. In another exemplary embodiment, more recently introduced micromachined capacitance transducer arrays such as may be built on a silicon wafer using MEMS (Micro Electro-Mechanical Systems) could be employed in lieu of the piezoelectric array. Micromachined capacitance ultrasonic transducer arrays usable for medical imaging applications are commercially available from Sensant Corporation. Regardless of the type of transducer, the vibratory energy is propagated through a medium undergoing ultrasonic imaging. For example, a transmit/receive switch 105 may be set to pass the excitation signal during a transmit mode of operation of the ultrasound system.

A plurality of interconnect channels, for simplicity of illustration only a single channel 106 is shown, enables optical communication of the ultrasonic probe with an imaging console 108. Each interconnect channel includes a quantum-well device 110, such as a SEED device, optically coupled to receive an electrical signal from a corresponding transducer, e.g., transducer 104. It will be appreciated that the electrical signal received by quantum-well device 110 is generated during a receive mode of operation of the ultrasound system in response to vibratory energy received from the medium undergoing imaging. The vibratory energy may comprise vibratory energy reflected from within the medium undergoing imaging or having passed through that medium. As discussed in the context of FIG. 3, quantum-well device 110 may comprise a three terminal device having a first terminal, e.g., gate terminal 112, a second terminal, e.g., source terminal 114 coupled to receive a biasing signal, and a third terminal, e.g., drain terminal 116 coupled to an electrical ground. In the embodiment illustrated in FIG. 4, gate terminal 112 is coupled to receive the electrical signal from transducer 104. However, as discussed in the context of FIG. 3, other connection arrangements for the respective three terminals may be used.

In one exemplary embodiment, an amplifier circuit 118 is coupled to provide a desired level of amplification to the electrical signal from each corresponding transducer prior to that electrical signal being supplied to the SEED device. As suggested above, the respective amplifier circuit 118 may comprise either a discrete circuit or may comprise an amplifier circuit jointly integrated with the SEED device, as represented by dashed rectangle 120. Examples of the amplifier circuit integrated with the SEED device include a complementary metal oxide semiconductor and a field effect transistor circuit.

As shown in FIG. 4, quantum well-device 110 is further configured to receive and process an input optical signal to supply a modulated output signal in response to amplitude variation of the electrical signal from transducer 104. In the embodiment of FIG. 5, a first optical cable assembly 122 is coupled to transmit from the imaging console the optical signal received by the quantum-well device. Cable assembly 122 is further coupled to transmit back to the imaging console the modulated signal supplied by the quantum-well device. A suitable optical source and detector module 126 in console 108 is used for generating the input optical signal beam and for processing the modulated signal supplied by quantum-well device through optical cable assembly 122. In another aspect of the present invention, a second cable assembly 124 is coupled to a phototransistor circuit 128 to transmit a control optical signal to control the firing of the high voltage excitation signal. In one exemplary implementation, an electrical cable 130 may continue to be used to carry the high voltage excitation signal used to excite the individual transducer elements.

As will be appreciated by those skilled in the art, reception of the reflected or echo signal is generally demanding since relatively high linearity of the individual elements/channels is desirable to allow high quality beamforming. Since the medium may attenuate the vibratory energy as a function of distance traveled, the echo signal may range in amplitude from about 100 mV to about 1 microV, for near and far targets respectively. Thus, instantaneous dynamic range in excess of 40 dB may be desirable. Since these echo signals should be preserved until the time delays can be applied in the console, it is desirable for the electrical to optical conversion to be substantially accurate and repeatable. The inventors of the present invention have recognized that the monolithic fabrication processes of SEED technology should lend themselves to meet these kinds of requirements.

In the event such 40 dB of dynamic range were not directly available from the SEED device and associated detecting circuitry, it will be appreciated that digital processing signal techniques may be used to digitize the information. See for example U.S. Pat. No. 5,203,335 assigned to the assignee of the present invention for background information regarding one example of such digital processing techniques. The referred patent titled "Phased Array Ultrasonic Beam Forming Using Oversampled A/D Converters" uses a high frequency delta-sigma converter to digitize the echo signal from each transducer element. It is further believed that the present invention allows to achieve the necessary digital bandwidth. For example, a 10 bit sampling at 40 MHz corresponds to approximately a 400 MHz digital rate. This type of requirement is well within the capabilities of the several GHz of bandwidth generally enabled by the SEED device.

It will be appreciated that various construction arrangements may be used for the SEED device. For example, one exemplary arrangement would have the SEED detector mounted directly on the back of the transducer array. In another exemplary arrangement, it may be desirable to mount packaged "chips" onto the flexible circuit board traditionally used for the linear transducer arrays. In this case, the fiber optic cables could then be coupled directly to the SEED device.

It will be understood that the specific embodiment of the invention shown and described herein is exemplary only. Numerous variations, changes, substitutions and equivalents will now occur to those skilled in the art without departing from the spirit and scope of the present invention. Accordingly, it is intended that all subject matter described herein and shown in the accompanying drawings be regarded as illustrative only and not in a limiting sense and that the scope of the invention be solely determined by the appended claims.

What is claimed is:

1. An ultrasound imaging system comprising:
    an ultrasonic probe including an array of ultrasonic transducers;
    a plurality of interconnect channels for enabling optical communication of the ultrasonic probe with an imaging console, each interconnect channel comprising:
        a quantum-well device having a terminal electrically coupled to receive an electrical signal from a corresponding transducer, the quantum well device further configured to receive and process an input optical signal to supply a modulated optical signal in response to amplitude variation of the electrical signal; and
        an optical cable assembly coupled to transmit from the imaging console the optical input signal received by the quantum-well device.

2. The ultrasound system of claim 1 wherein said optical cable assembly is further coupled to transmit back to the imaging console the modulated signal supplied by the quantum well device.

3. The ultrasound system of claim 1 wherein the array of ultrasonic transducers comprises an array of piezoelectric transducers.

4. The ultrasound system of claim 1 wherein the array of ultrasonic transducers comprises an array of micromachined capacitance transducers.

5. The ultrasound system of claim 1 wherein the quantum-well device comprises a self-electro-optic effect (SEED) device.

6. The ultrasound system of claim 5 further comprising a respective amplifier circuit coupled to provide a desired level of amplification to the electrical signal from each corresponding transducer.

7. The ultrasound system of claim 6 wherein the respective amplifier circuit comprises a circuit selected from the group consisting of a complementary metal oxide semiconductor and a field effect transistor.

8. The ultrasound system of claim 6 wherein the amplifier circuit and the SEED device comprise an integrated circuit.

9. The ultrasound system of claim 6 wherein the terminal comprises a first terminal and wherein the SEED device further comprises second and third terminals, one of said second and third terminals connected to receive a biasing signal and the other one of said second and third terminals connected to an electrical ground.

10. The ultrasound system of claim 9 wherein the first terminal corresponds to a gate terminal, the second terminal corresponds to a source terminal and is connected to the biasing signal, and the third terminal corresponds to a drain terminal and is connected to the electrical ground.

11. The ultrasound system of claim 9 wherein the first terminal corresponds to a source terminal, the second terminal corresponds to a gate terminal and is connected to the biasing signal, and the third terminal corresponds to a drain terminal and is connected to the electrical ground.

12. The ultrasound system of claim 1 wherein said optical cable assembly comprises a first optical cable assembly and further comprising a second optical cable assembly coupled to a phototransistor circuit responsive to an optical control signal transmitted through said second optical cable assembly to generate an excitation electrical signal.

13. The ultrasound system of claim 12 wherein said excitation electrical signal is transmitted to a corresponding transducer to cause the transducer to generate vibratory energy to be propagated through a medium during a transmit mode of operation of the ultrasound system.

14. The ultrasound system of claim 13 wherein the electrical signal received by the quantum-well device from each corresponding transducer is generated during a receive mode of operation of the ultrasound system in response to vibratory energy received from within the medium.

15. An optical interconnect for an ultrasound imaging system having an ultrasonic probe including an array of ultrasonic transducers, said interconnect comprising:
    a plurality of interconnect channels for enabling optical communication of the ultrasonic probe with an imaging console, each interconnect channel comprising:
        a quantum-well device having a terminal electrically coupled to receive an electrical signal from a corresponding transducer, the quantum well device further configured to receive and process an input optical signal to supply a modulated optical signal in response to amplitude variation of the electrical signal; and
        an optical cable assembly coupled to transmit from the imaging console the optical input signal received by the quantum-well device, said optical cable assembly further coupled to transmit back to the imaging console the modulated signal supplied by the quantum well device.

16. The optical interconnect of claim 15 wherein the quantum-well device comprises a self-electro-optic effect (SEED) device.

17. The optical interconnect of claim 15 wherein said optical cable assembly comprises a first optical cable assembly and further comprising a second optical cable assembly coupled to a phototransistor circuit responsive to an optical control signal transmitted from the console through said second optical cable assembly to generate a respective excitation electrical signal, wherein said excitation electrical signal is transmitted to a corresponding transducer to cause the transducer to generate vibratory energy to be propagated through a medium during a transmit mode of operation of the ultrasound system, and further wherein the electrical signal received by the quantum-well device from each corresponding transducer is generated during a receive mode of operation of the ultrasound system in response to vibratory energy received from within the medium.

18. The optical interconnect of claim 16 further comprising a respective amplifier circuit coupled to provide a desired level of amplification to the electrical signal from each corresponding transducer.

19. The optical interconnect of claim 18 wherein the respective amplifier circuit comprises a circuit selected from the group consisting of a complementary metal oxide semiconductor and a field effect transistor.

20. The optical interconnect of claim 18 wherein the amplifier circuit and the SEED device comprise an integrated circuit.

21. The optical interconnect of claim 18 wherein the terminal comprises a first terminal and wherein the SEED device comprises second and third terminals, one of said second and third terminals connected to receive a biasing signal and the other one of said second and third terminals connected to an electrical ground.

22. The optical interconnect of claim 21 wherein the first terminal corresponds to a gate terminal, the second terminal corresponds to a source terminal and is connected to the biasing signal, and the third terminal corresponds to a drain terminal and is connected to the electrical ground.

23. The optical interconnect of claim 21 wherein the first terminal corresponds to a source terminal, the second terminal corresponds to a gate terminal and is connected to the biasing signal, and the third terminal corresponds to a drain terminal and is connected to the electrical ground.

24. A method for optically interconnecting an ultrasound imaging system having an ultrasonic probe including an array of ultrasonic transducers, said method comprising:
  enabling optical communication of the ultrasonic probe with an imaging console through a plurality of interconnect channels, for each interconnect channel the optical communication enabled by;
    electrically coupling a quantum-well device to receive an electrical signal from a corresponding transducer,
    optically coupling the quantum well device to receive and process an input optical signal to supply a modulated optical signal in response to amplitude variation of the electrical signal,
    providing an optical cable assembly to transmit from the imaging console the optical input signal received by the quantum-well device, and
    optically coupling said optical cable assembly to transmit back to the imaging console the modulated signal supplied by the quantum well device.

25. The method of claim 24 wherein said optical cable assembly comprises a first optical cable assembly and further comprising optically coupling a second optical cable assembly to a phototransistor circuit responsive to an optical control signal transmitted from the console through said second optical cable assembly to generate a respective excitation electrical signal, wherein said excitation electrical signal is transmitted to a corresponding transducer to cause the transducer to generate vibratory energy to be propagated through a medium during a transmit mode of operation of the ultrasound system, and further wherein the electrical signal received by the quantum-well device from each corresponding transducer is generated during a receive mode of operation of the ultrasound system in response to propagated vibratory energy received from within the medium.

* * * * *